(12) United States Patent
Isaka et al.

(10) Patent No.: US 7,414,069 B2
(45) Date of Patent: Aug. 19, 2008

(54) ANTITUBERCULOSIS COMPOUNDS, HIRSUTELLONES A, B, AND C

(75) Inventors: Masahiko Isaka, Bangkok (TH); Nigel Leslie Hywel-Jones, Bangkok (TH); Sayanh Somrithipol, Pathumthani (TH); Kanyawim Kirtikara, Pathumthani (TH); Prasit Palittapongarnpim, Bangkok (TH); Yodhathai Thebtaranonth, Pathumthani (TH)

(73) Assignee: National Center for Genetic Engineering & Biotechnology, National Science & Technology Development Agency, Pathumthani (TH)

( * ) Notice: Subject to any disclaimer, the term of this patent is extended or adjusted under 35 U.S.C. 154(b) by 204 days.

(21) Appl. No.: 11/285,522

(22) Filed: Nov. 21, 2005

(65) Prior Publication Data

US 2006/0122252 A1    Jun. 8, 2006

(30) Foreign Application Priority Data

Nov. 23, 2004    (TH) ..................... 095611

(51) Int. Cl.
*A61K 31/407*    (2006.01)
*C07D 491/04*    (2006.01)
*C12P 17/00*    (2006.01)

(52) U.S. Cl. ................ 514/410; 435/117; 548/417
(58) Field of Classification Search .......... 514/410; 435/117; 548/417
See application file for complete search history.

(56) References Cited

FOREIGN PATENT DOCUMENTS

JP    2001247574    9/2001

OTHER PUBLICATIONS

Isaka et al. "Hirsutellones A-E, antimycobacterial alkaloids from the insect pathogenic fungus *Hirsutella nivea* BCC 2594" Tetrahedron, 2005, vol. 61, pp. 5577-5583.*
Collins, Lisa A. et al. (May 1997) "Microplate Alamar Blue Assay versus BACTEC 460 System for High-Throughput Screening of Compounds against *Mycobacterium tuberculosis* and *Mycobacterium avium*," Antimicrobial Agents and Chemotherapy, 41(5): 1004-1009.
He, Haiyin et al. (2002) "Pyrrocidines A and B, new antibiotics produced by a filamentous fungus," Tetrahedron Letters, 43: 1633-1636.
Hywel-Jones, Nigel L. (1997) "*Hirsutella* species associated with hoppers (Homoptera) in Thailand," Mycol. Res., 101(10): 1202-1206.
Skehan, Philip et al. (Jul. 4, 1990) "New Colorimetric Cytotoxicity Assay for Anticancer-Drug Screening," Natl Cancer Inst, 82(13): 1107-1112.

* cited by examiner

*Primary Examiner*—Rei-tsang Shiao
*Assistant Examiner*—Joseph R Kosack
(74) *Attorney, Agent, or Firm*—Morrison & Foerster LLP

(57) ABSTRACT

Three new alkaloids, Hirsutellones A, B, and C, are produced in cultures of fungus such as *Hirsutella nivea* strain BCC 2594 and *Trichoderma* sp. strain BCC 7579. The Hirsutellones exhibited potent growth inhibitory activity against *Mycobacterium tuberculosis* (H37Ra strain) with an MIC value of 0.78 μg/ml, while showing weak or no cytotoxicity to mammalian cells. Therefore, Hirsutellones and pharmaceutical compositions containing Hirsutellones may be useful for the treatment of tuberculosis. Also described herein are methods of isolating the Hirsutellones.

24 Claims, 12 Drawing Sheets

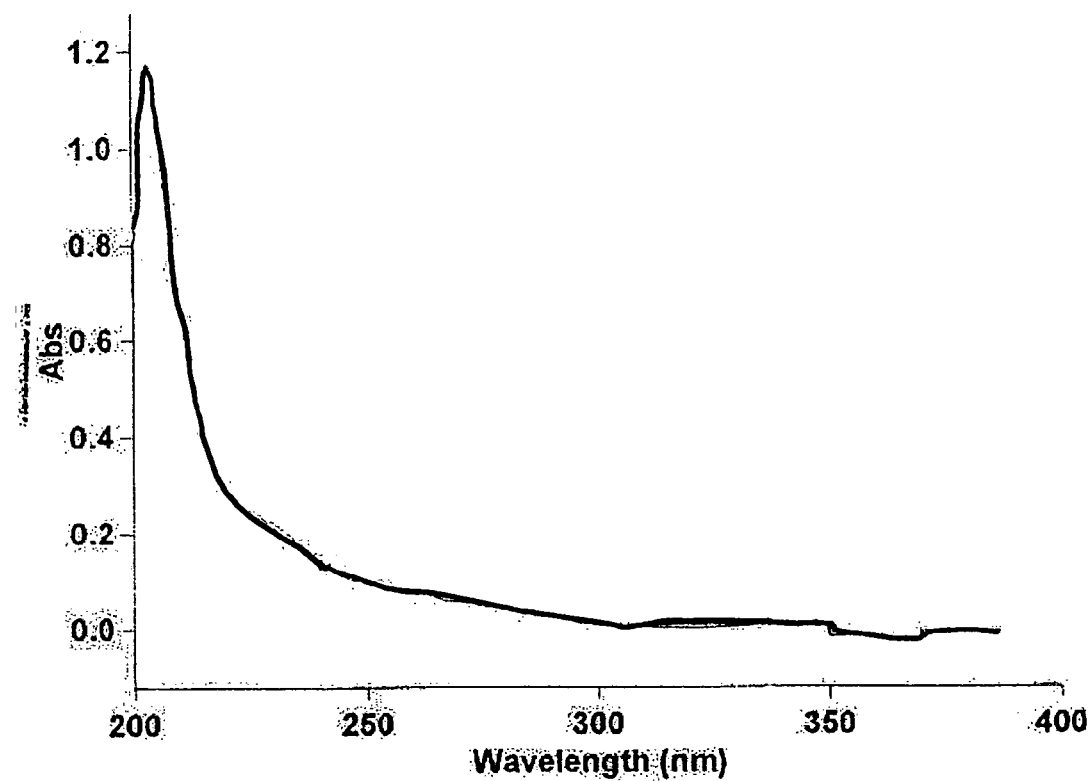
FIG. 1. UV absorption spectrum of hirsutellone A (20 µg/ml solution in methanol)

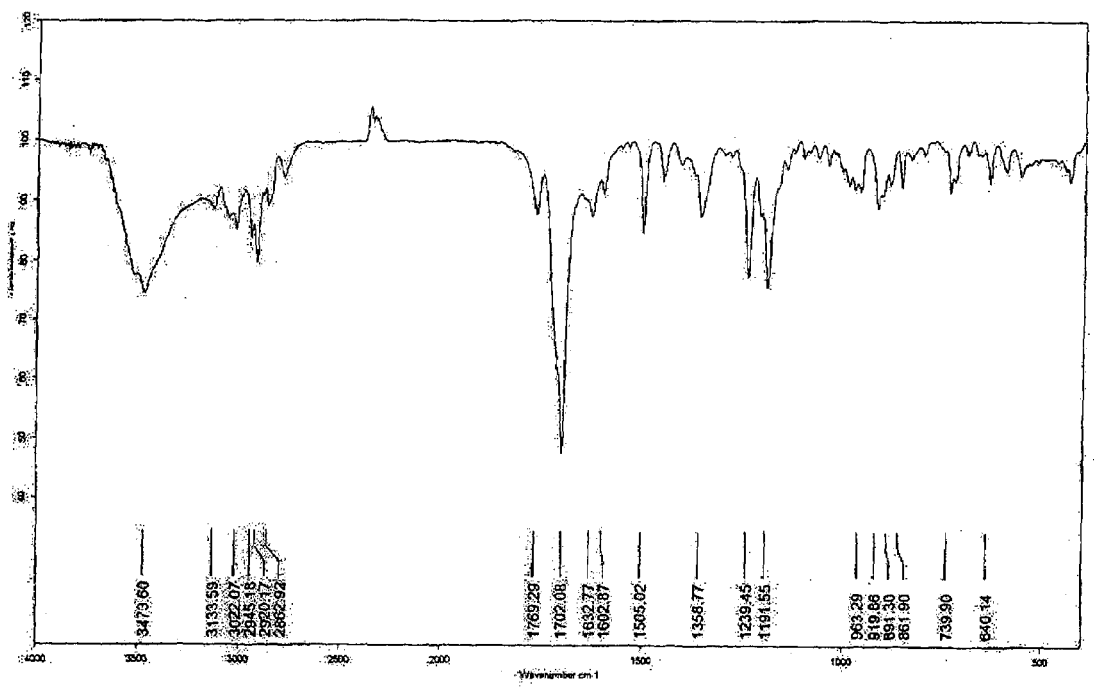
FIG. 2. IR absorption spectrum of hirsutellone A (KBr disk)

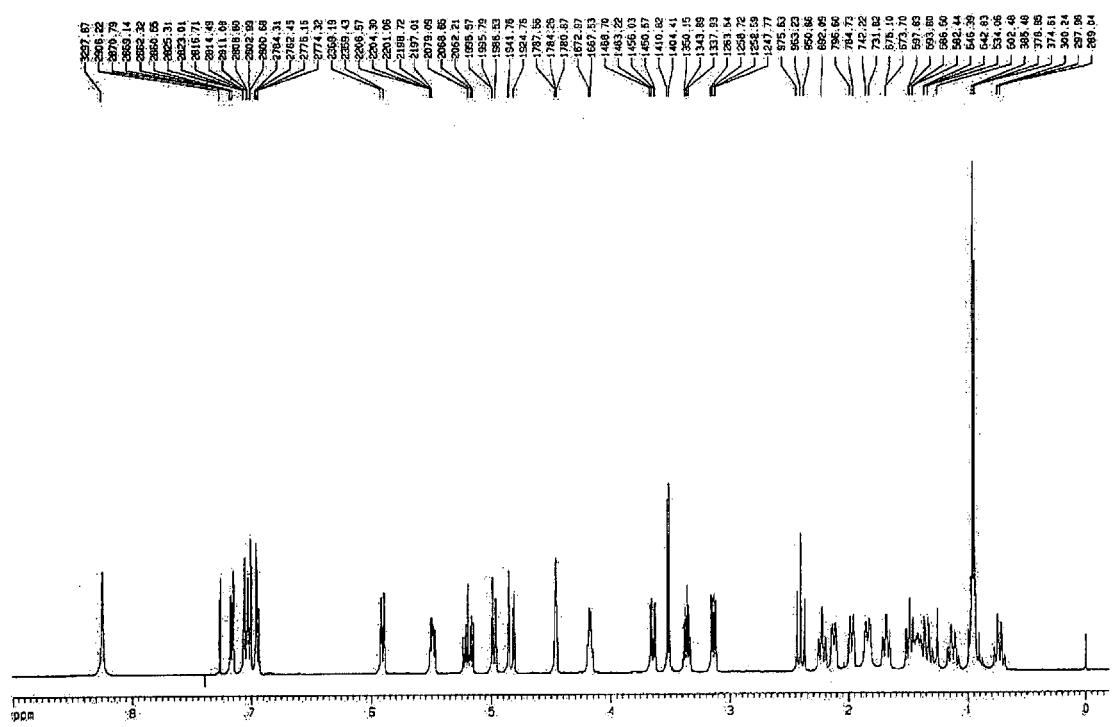
FIG. 3. $^1$H NMR spectrum of hirsutellone A (400 MHz, CDCl$_3$)

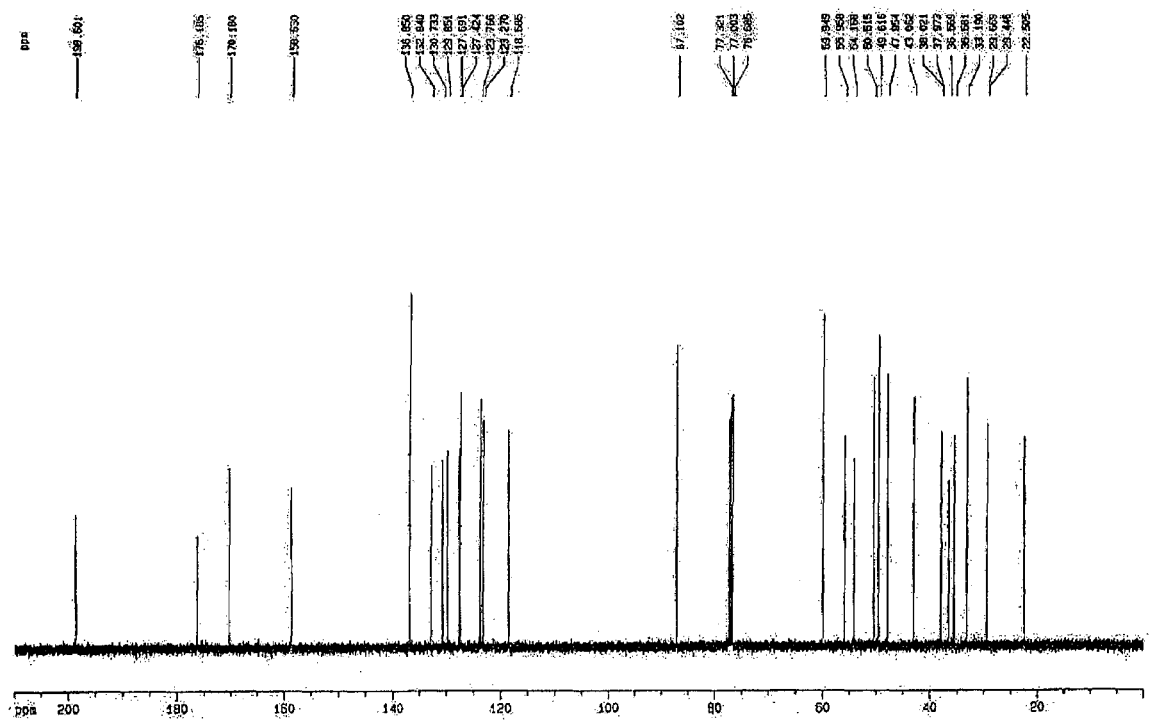
FIG. 4. $^{13}$C NMR spectrum of hirsutellone A (100 MHz, CDCl$_3$)

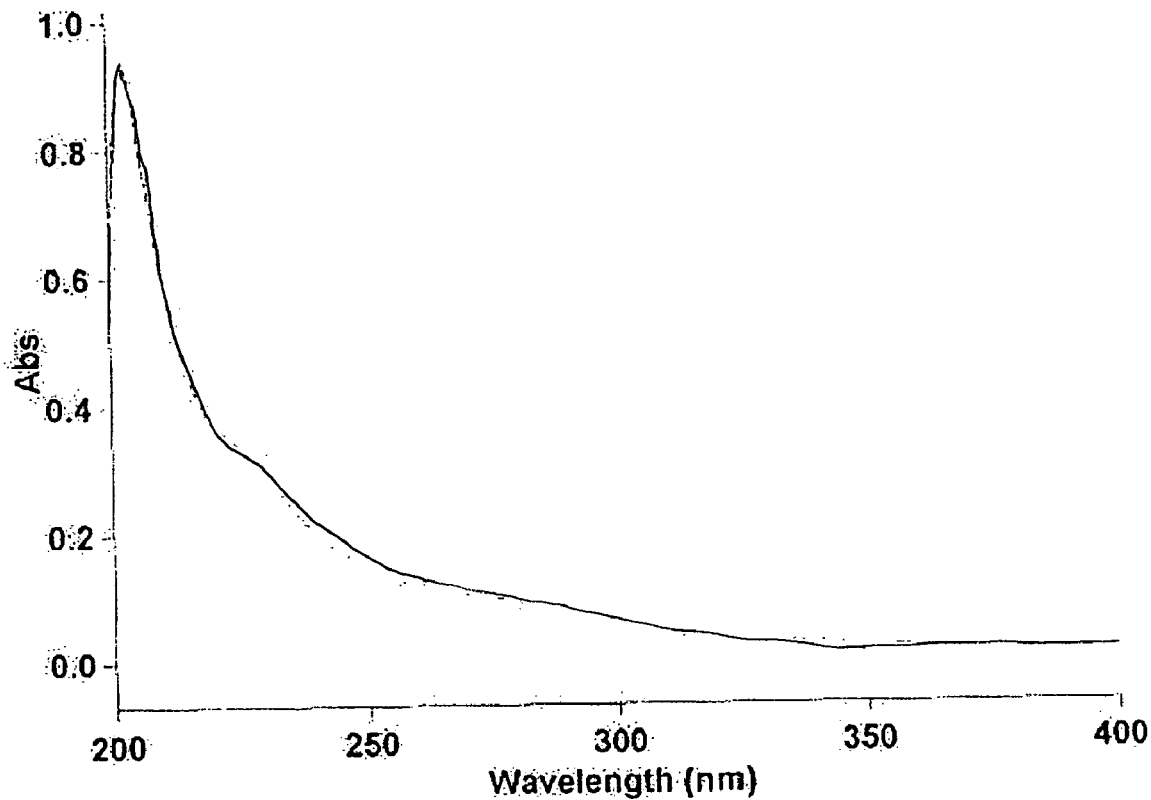
FIG. 5. UV absorption spectrum of hirsutellone B (20 µg/ml solution in methanol)

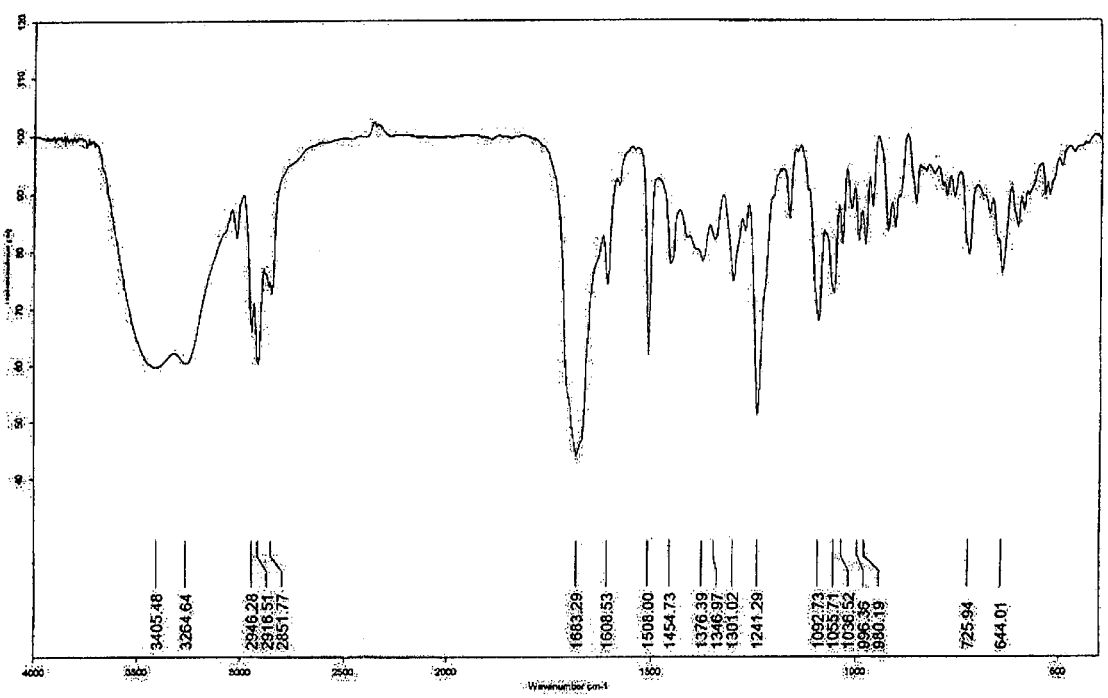
FIG. 6. IR absorption spectrum of hirsutellone B (KBr disk)

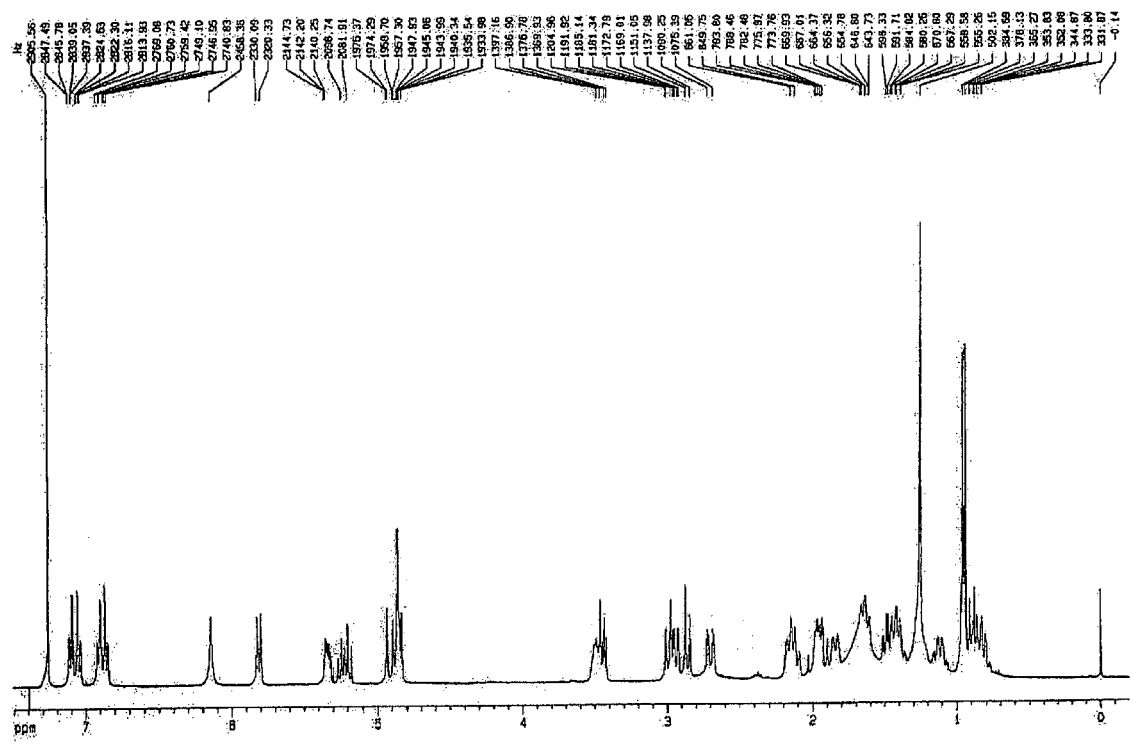
FIG. 7. $^1$H NMR spectrum of hirsutellone B (400 MHz, CDCl$_3$)

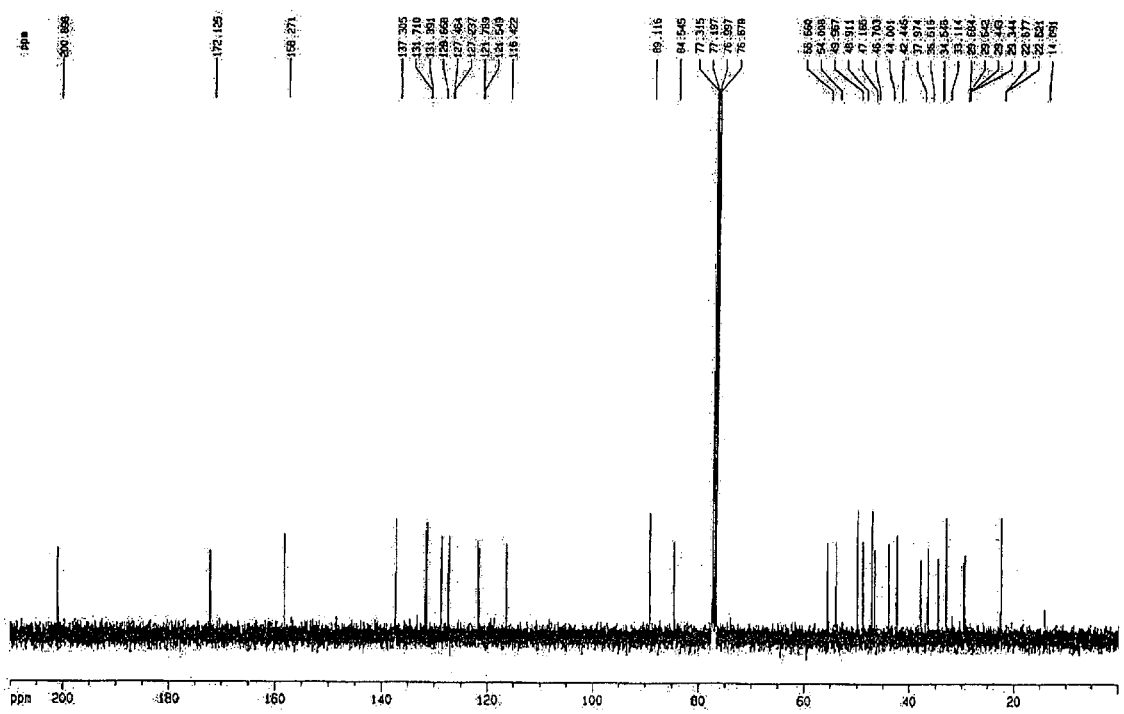
FIG. 8. $^{13}$C NMR spectrum of hirsutellone B (100 MHz, CDCl$_3$)

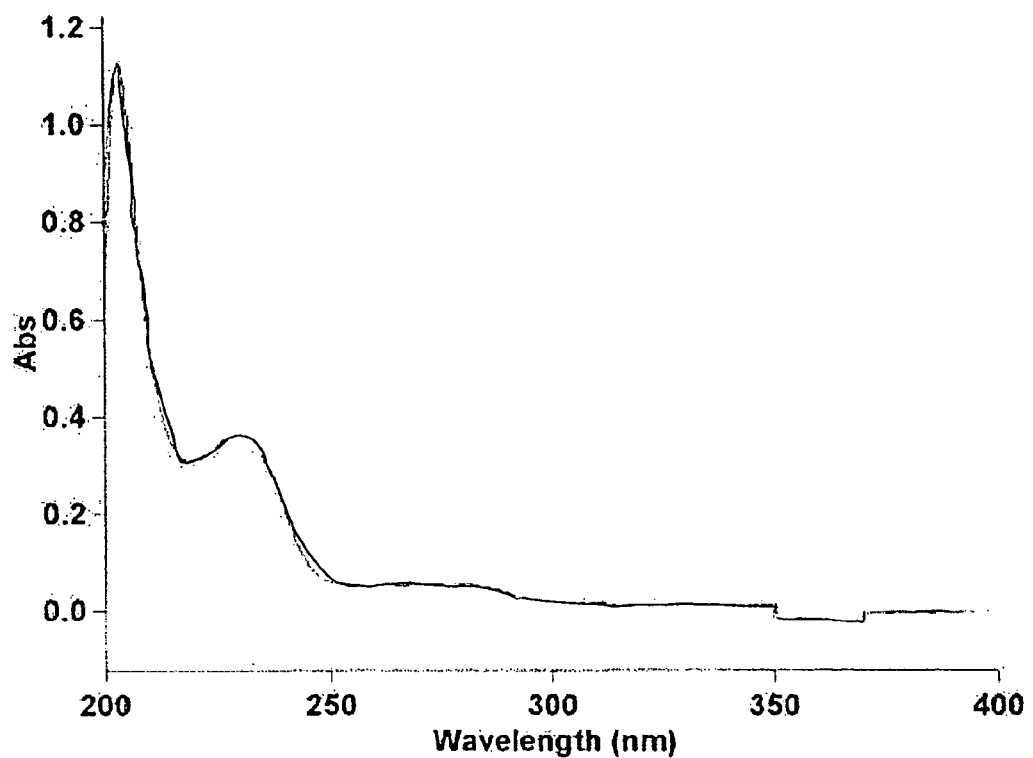
FIG. 9. UV absorption spectrum of hirsutellone C (20 µg/ml solution in methanol)

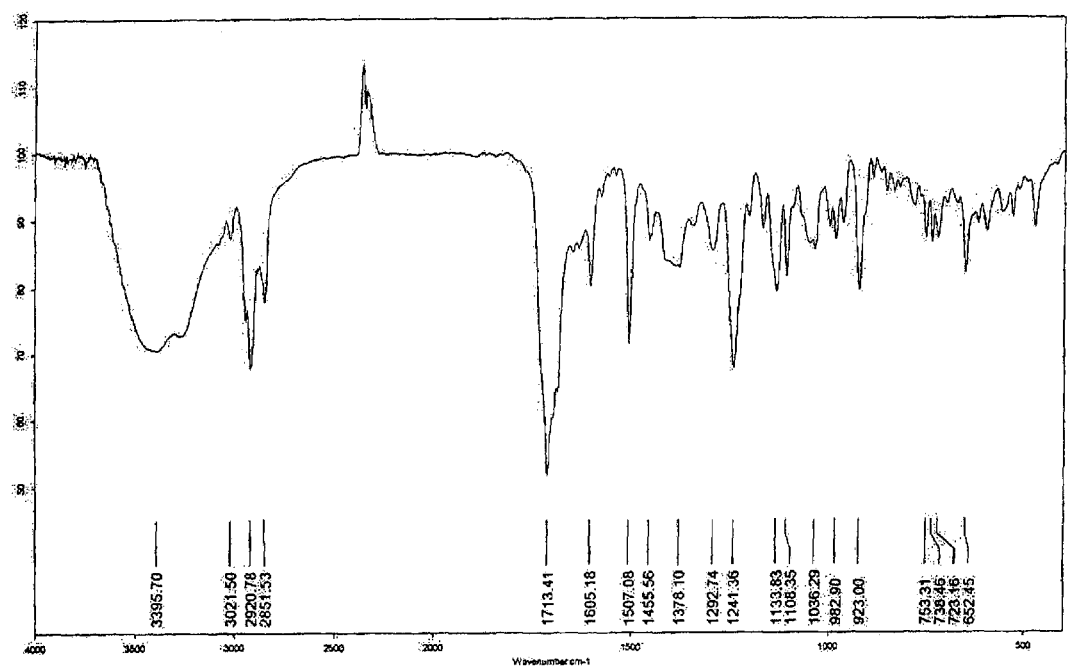
FIG. 10. IR absorption spectrum of hirsutellone C (KBr disk)

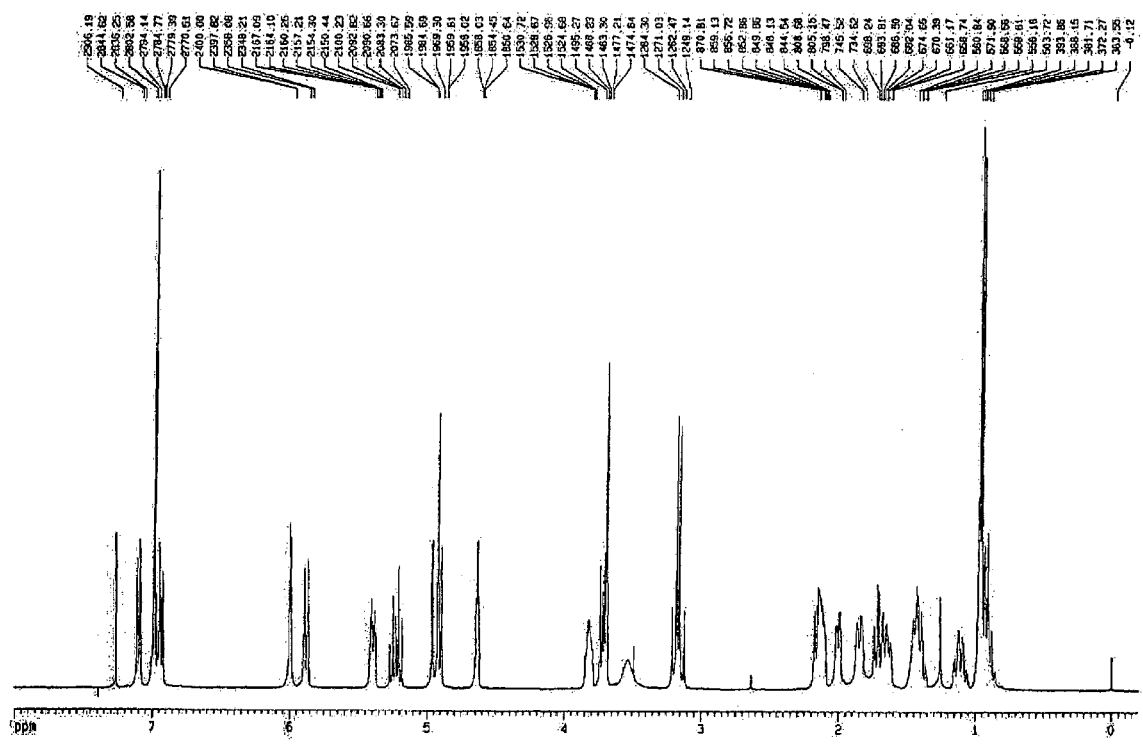
FIG. 11. ¹H NMR spectrum of hirsutellone C (400 MHz, CDCl₃)

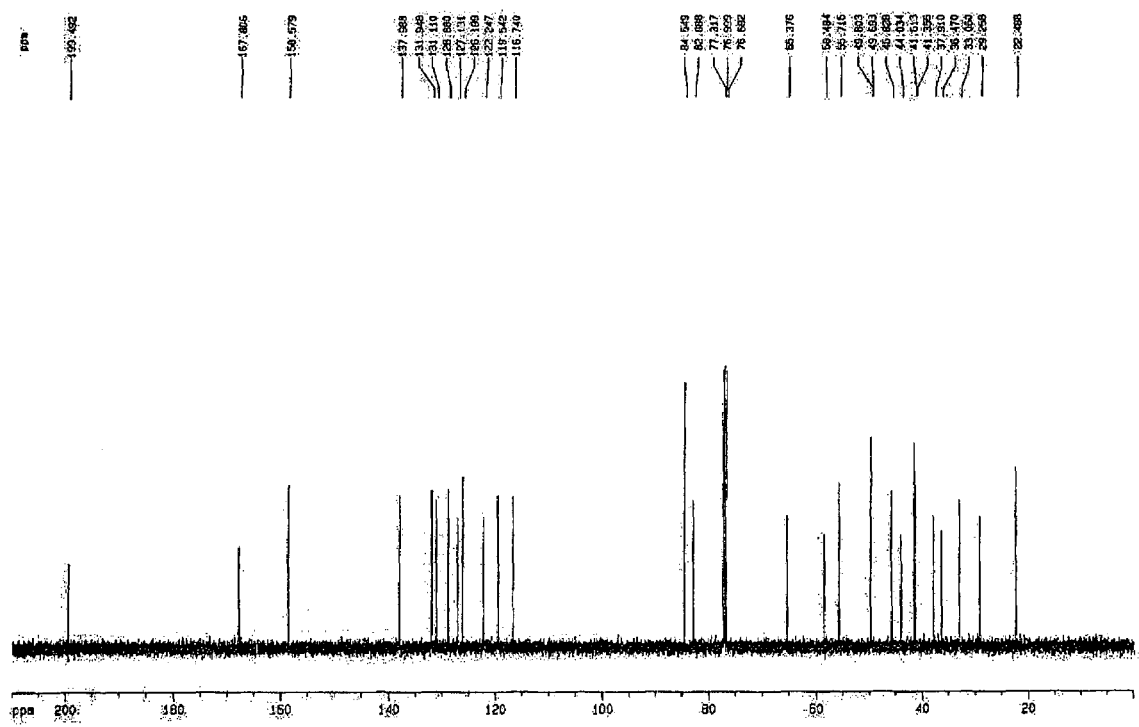
FIG. 12. $^{13}$C NMR spectrum of hirsutellone C (100 MHz, CDCl$_3$)

ANTITUBERCULOSIS COMPOUNDS, HIRSUTELLONES A, B, AND C

CROSS REFERENCE TO RELATED APPLICATIONS

This application claims priority to Thai Application No. 095611 under 35 U.S.C. 119(a), filed Nov. 23, 2004, the entire content of which is incorporated by reference herein as if fully put forth below.

FIELD OF THE INVENTION

The present invention relates generally to new antituberculosis compounds designated Hirsutellones A, B and C, and to their production by fermentation. The compounds of the present invention, as well as pharmaceutical compositions containing the compounds, find use as drugs for the treatment of tuberculosis.

BACKGROUND OF THE INVENTION

Tuberculosis, caused by the bacterium *Mycobacterium tuberculosis*, is an important communicable disease worldwide. *Mycobacterium* is a genus of bacteria which has special cell membrane structures different from other bacteria. This renders most antibiotics unable to enter the bacterial cells, leading to the failure of antibiotics to inhibit the growth of the bacteria. Tuberculosis, therefore, requires special drugs for treatment.

Anti-tuberculosis drugs can be divided into two groups. The first line drugs are highly effective and of relatively low toxicity. The second line drugs are less effective and/or of relatively high toxicity, and are used when the bacteria resist the first line drugs. There are five first line drugs, which are isoniazid, rifampin, pyrazinamide, ethambutol and streptomycin. Standard tuberculosis treatment requires four of these drugs which normally include isoniazid and rifampin with two other drugs, usually pyrazinamide and ethambutol or streptomycin. The six month treatment starts with these four drugs for two months, followed by treatment with isoniazid and rifampin for four months. This is because only isoniazid and rifampin are highly effective in killing the bacteria. When *M. tuberculosis* shows resistance to either pyrazinamide, ethambutol or streptomycin, the treatment requires the switch to the second line drugs but the patient may still be able to complete the treatment within six months. On the other hand, if the organisms are resistant to isoniazid or rifampin, even the switch to other effective drugs may not render successful treatment within six months. The treatment may need to be lengthened up to eighteen months especially if the organisms resist rifampin.

*M. tuberculosis* is considered a multi-drug resistant strain when it resists both isoniazid and rifampin. Multi-drug resistant tuberculosis is a very serious public health problem because it cannot be cured during the normal course of treatment or perhaps not at all. This is due to the fact that the bacteria have developed resistance to other drugs during the treatment. The patients may have no serious symptoms even though the treatment cannot eliminate the bacteria because the drugs may have control over the organisms to some extent. The patients can therefore transmit the resistant strains to other people.

The limited number of highly effective drugs is a major problem in tuberculosis control. Although isoniazid and rifampin were discovered over 30 years ago, resistant strains have since emerged. There is thus a need to identify new and effective drugs against *Mycobacterium tuberculosis*.

SUMMARY OF SOME FEATURES OF THE INVENTION

In order to meet this need, three antimycobacterial compounds are described, designated as Hirsutellones A, B and C. The structures for these compounds are as follows:

Hirsutellone A:

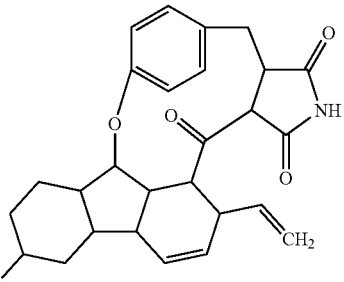

Hirsutellone B:

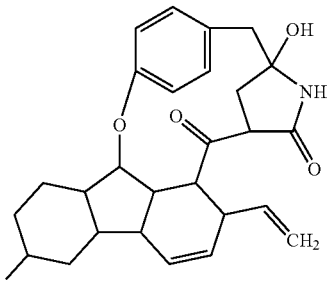

Hirsutellone C:

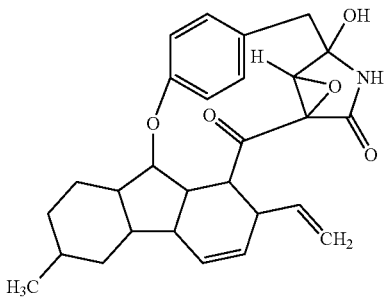

Also described are methods of isolating the Hirsutellones. The Hirsutellones may be obtained by fermentation of a fungus such as the fungal strain BCC 2594, which was identified as *Hirsutella nivea* (Ascomycota: Hypocreales: asexual Clavicipitaceae), or the fungal strain BCC 7579, which was identified as *Trichoderma* sp. (Ascomycota: Hypocreales: asexual Hypocreaceae).

Disclosed herein are methods of producing the Hirsutellones comprising fermenting a liquid culture of a fungus, for example the fungal strains BCC 2594 or BCC 7579, isolating mycelia from said culture, extracting the mycelia with an organic solvent to produce an extract, and separating the extract to produce an antimycobacterial compound. The mycelia can be isolated by filtration, and the extract can be separated by gel filtration or chromatography.

Also described is a method for treating tuberculosis in a subject by administering to the subject an effective amount of a pharmaceutical formulation containing at least one of the Hirsutellones or a pharmaceutically acceptable derivative or salt thereof, and a pharmaceutically acceptable carrier therefor.

BRIEF DESCRIPTION OF THE DRAWINGS

FIG. 1 shows a UV absorption spectrum of Hirsutellone A (20 µg/ml solution in methanol).

FIG. 2 shows an IR absorption spectrum of Hirsutellone A (KBr disc).

FIG. 3 shows a 1H-NMR spectrum of Hirsutellone A (400 MHz, CDCl3).

FIG. 4 shows a 13C-NMR spectrum of Hirsutellone A (100 MHz, CDCl3).

FIG. 5 shows a UV absorption spectrum of Hirsutellone B (20 µg/ml solution in methanol).

FIG. 6 shows an IR absorption spectrum of Hirsutellone B (KBr disc).

FIG. 7 shows a 1H-NMR spectrum of Hirsutellone B (400 MHz, CDCl3).

FIG. 8 shows a 13C-NMR spectrum of Hirsutellone B (100 MHz, CDCl3).

FIG. 9 shows a UV absorption spectrum of Hirsutellone C (20 µg/ml solution in methanol).

FIG. 10 shows an IR absorption spectrum of Hirsutellone C (KBr disc).

FIG. 11 shows a 1H-NMR spectrum of Hirsutellone C (400 MHz, CDCl3).

FIG. 12 shows a 13C-NMR spectrum of Hirsutellone C (100 MHz, CDCl3).

DETAILED DESCRIPTION OF THE INVENTION

It is to be understood that the invention is not limited in its application to the details of construction and the arrangement of the components set forth in the following description. The invention is capable of other embodiments or of being practiced or carried out in various ways. Also, it is to be understood that the phraseology and terminology employed herein is for the purpose of description and should not be regarded as limiting.

Described herein are compounds of the following formulas.

Hirsutellone A:

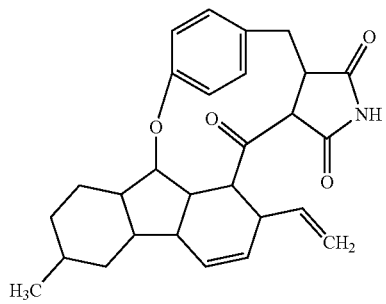

Hirsutellone B:

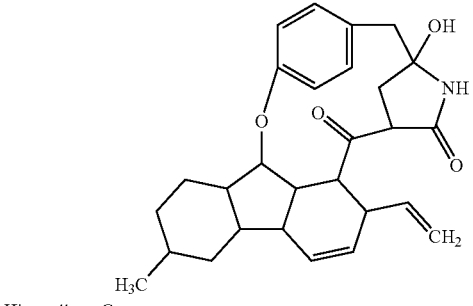

Hirsutellone C:

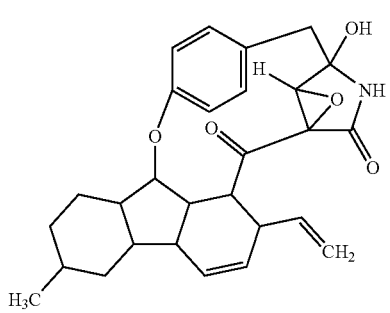

Antimycobacterial activity of this chemical class of compounds has not been previously reported.

Also described are methods of isolating the above compounds, as explained in more detail below.

General Fermentation Conditions Cultivation of fungal strains, such as BCC 2594 or BCC 7579, which produce the Hirsutellones, may be carried out in a wide variety of liquid culture media. In general, media which are useful for the production of Hirsutellones contain assimilable sources of carbon, such as starch, sugar, molasses, glycerol, etc.; assimilable sources of nitrogen such as amino acids, polypeptides, protein, etc., as well as complex sources such as yeast extract, malt extract, peptone, corn steep liquor, etc.; and inorganic salts such as NaCl, KCl, $MgSO_4$, $KH_2PO_4$, $Na_2HPO_4$, $FeSO_4$, $CaCO_3$, etc. Trace elements such as $MnCl_2$, $CoCl_2$, $ZnSO_4$, $CaSO_4$, etc. may also be used. These inorganic salts are sometimes important for fungal growth and metabolite production. An anti-foaming agent such as silicone or polyethylene glycol may be added as needed.

The preferred process for production of Hirsutellones consists of inoculating mycelia or spores of the producing organism into a suitable liquid medium and then cultivating them under aerobic conditions.

The general fermentation procedure is to first inoculate a preserved source of culture into a nutrient seed medium, such as Potato Dextrose Broth, and to obtain, sometimes through a two-step process, growth of the fungus which serves as seed in the production of the active compounds. After inoculation, the flasks are incubated under agitation, preferably 200 to 220 rpm, at temperatures ranging from 20° C. to 30° C., preferably 25° C. to 28° C. Seed flasks are incubated 2 to 15 days. A second stage seed growth may be employed, in this case involving larger vessels or using large numbers of flasks.

Portions of the seed cultures are transferred into flasks containing suitable production medium. Preferably, the volume of the production medium is approximately 10 times the volume of the seed culture. The fermentation is conducted either under agitation or static conditions for 10 to 80 days at temperatures ranging from 20° C. to 30° C., preferably 25° C. to 28° C. After an appropriate period for production of the desired compounds, fermentation products are harvested and active compounds isolated.

General Procedure for the Isolation and Separation of Hirsutellones

Most of the Hirsutellones present in the fermentation of a fungus such as BCC 2594 or BCC 7579 are associated with the cell mass and can be extracted from the mycelial cake by an organic solvent such as methanol, ethanol, acetone, 2-butanone, dichloromethane, ethyl acetate, diethyl ether, or a mixture of two or more of these solvents. The extract from mycelia which contains the Hirsutellones can be separated and purified by standard chromatographic methods using adsorbents such as Sephadex™ LH-20 and silica gel. This purification method results in a product which is substantially purified. Gel filtration with Sephadex™ LH-20 is useful for the partial purification of the hirsutanones mixture, wherein fatty acids and other substances can be removed. Preferred eluents for the gel filtration are methanol or a methanol-dichloromethane mixture. Silica gel, such as that available from MERCK, is the preferred adsorbent for the separation of the Hirsutellones. When silica gel is the absorbent, methanol-dichloromethane or ethyl acetate-dichloromethane is useful as an eluent. When the separation of the compounds is not completely achieved by silica gel column chromatography, preparative reversed-phase column using C18 bonded silica is useful for further purification, preferably, employing the equipment of high-performance liquid chromatography (HPLC). One example of a useful absorbent for preparative HPLC is Nova-Pak® HR C18 (6 µm, 40×100 mm), a product of Waters containing C18 bonded silica. As a mobile phase, it is possible to use a mixture of acetonitrile or methanol and water.

Also described herein are pharmaceutical compositions containing the Hirsutellones, for use in the treatment of tuberculosis. Hirsutellones may be administered either alone or, preferably, in combination with pharmaceutically acceptable carriers or diluents, optionally with known adjuvants, such as alum, in a pharmaceutical composition, according to standard pharmaceutical practice. The compounds can be administered orally or parenterally, including the intravenous, intramuscular, intraperitoneal, subcutaneous, rectal and topical routes of administration.

For oral use of a compound according to the disclosure herein, the selected compounds may be combined with a physiologically compatible excipient or carrier and administered, for example, in the form of tablets or capsules, or as an aqueous solution or suspension. In the case of tablets for oral use, carriers which are commonly used include lactose and cornstarch, and lubricating agents, such as magnesium stearate, are commonly added. For oral administration in the capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

Also described herein is the use of the Hirsutellones and compositions containing Hirsutellones in the treatment of tuberculosis.

In describing and claiming the present invention, the following terminology will be used in accordance with the definitions set out below.

As used in the specification and the claims, the singular forms "a", "an", and "the" include plural referents unless the context clearly dictates otherwise, As used herein, "effective amount" means an amount of drug or pharmacologically active agent that is sufficient to provide the desired local or systemic effect and performance in a subject at a reasonable benefit to risk ratio. An effective amount of the compounds of the present invention is an amount sufficient to reduce the numbers of a *Mycobacterium* species in a subject.

As used herein, a "pharmaceutically acceptable carrier" component is one that is suitable for use without undue side effects (such as toxicity, irritation, and allergic response) commensurate with a reasonable benefit to risk ratio.

Applicants have made available to the public without restriction a deposit of fungal strains having accession numbers BCC 2594 and BCC 7579 at the Thailand BIOTEC Culture Collection (BCC), National Center for Genetic Engineering and Biotechnology, BIOTEC Central Research Unit, 113 Thailand Science Park, Phaholyothin Road, Klong 1, Klongluang, Pathumthani 12120, Thailand. The deposit will be maintained in the BCC, and will be replaced if a deposit becomes nonviable during that period. The deposits will be made available to the public upon granting of the patent, based on this application.

EXAMPLES

Example 1

Preparation of Hirsutellones by Fermentation of *Hirsutella nivea* BCC 2594

Background *Hirsutella nivea* was described as a new species from leaf-hoppers (Homoptera: Cicadellidae) (Hywel-Jones N. L., Mycol. Res., 101: 1202-1206 (1997)) and was based on a specimen (NHJ665.01) collected from Khao Yai National Park in Thailand (Dec. 12, 1991). Collections at the time of publication yielded no viable cultures. Isolate BCC2594 was secured from conidia of a single specimen. Collection details were as follows.

The specimen was classified as phylum Ascomycota, class Mitosporic, order Hypocreales, family Clavicipitaceae, genus *Hirsutella*, species *nivea*. This fungus was deposited on Mar. 2, 2000 at the Thailand BIOTEC Culture Collection (BCC), National Center for Genetic Engineering and Biotechnology, BIOTEC Central Research Unit, 113 Thailand Science Park, Phaholyothin Road, Klong 1, Klongluang, Pathumthani 12120, Thailand, as accession number BCC 2594.

*Hirsutella nivea*, BCC 2594, covers the host insect with a thin white film of mycelium which spreads over the leaf surface fixing the insect to the leaf. Usually a single (rarely two) slender synnema emerges from between the head and thorax of the insect and grows to a length of 8-13 mm. The sporulating structures (conidiogenous cells with phialides) are located along the synnema. A unique feature of this species, compared with other members of the genus is the pure white color.

BCC 2594 was isolated onto Potato Dextrose Agar (PDA) by wiping conidia from a single erect synnema developing from between the head and thorax of the infected host. The description of the fungus on the host is as given by Hywel-Jones (1997) for the type specimen. This specimen and all subsequent specimens match closely with the description of the type specimen (NHJ665.01), and are therefore considered to be the same species.

Cultures were secured from conidia germinating on PDA. These cultures were slow-growing (30 mm in 28 days at 25° C.) on PDA, and were composed of a sterile, white mycelium with hyphae measuring 2-3 μm. Hywel-Jones (1997) recorded the stroma on the insect as 'covering the insect in a compact white film'. Although attempts to induce sporulation failed, the compact, white filmy appearance was mimicked in axenic cultures on PDA. Cultural characteristics including slow growth with a white sterile mycelium fit with other insect-pathogenic members of the Clavicipitaceae.

Experimental Procedures BCC 2594 was maintained on Potato Dextrose Agar at 25° C. for 16 days, which was cut into pieces (1×1 cm) and inoculated into 4×250 ml Erlenmeyer flasks containing 25 ml of Difco™ Potato Dextrose Broth (PDB; composition, potato starch 4.0 g, dextrose 20.0 g, per liter) (8 pieces for each flask). After incubation at 25° C. for 8 days on a rotary shaker (200 rpm), each primary culture was transferred into a 1 liter Erlenmeyer flask containing 250 ml of the same liquid medium (PDB), and incubated at 25° C. for 8 days on a rotary shaker (200 rpm). Each 25 ml portion of the secondary cultures (in 4 flasks) was transferred into 32×1 liter Erlenmeyer flasks each containing minimum salt medium (composition; glucose 20.0 g, $NH_4NO_3$ 3.0 g, $KH_2PO_4$ 0.5 g, $MgSO_4·7H_2O$ 0.5 g, $CaCl_2$ 0.5 g and yeast extract 1.0 g, per liter), and static fermentation was carried out at 25° C. for 40 days.

The cultures were filtered and the residues (wet mycelia) were extracted with 1000 ml of methanol at room temperature for 2 days. After filtration, $H_2O$ (50 ml) was added to the filtrate, and partitioned between hexane (400 ml). The aqueous methanol layer was separated from the hexane layer, and concentrated under reduced pressure. The residual oil was dissolved in ethyl acetate (500 ml), washed with $H_2O$ (150 ml), and concentrated to obtain a brown gum (1.57 g). This mycelial extract was passed through a Sephadex LH-20 column (3×25 cm; methanol as eluent).

Fractions containing Hirsutellones were combined and subjected to column chromatography on silica gel (methanol/dichloromethane, step gradient elution) to obtain three fractions; Fr-A (contained Hirsutellone A, 140 mg), Fr-B (contained Hirsutellone C, 35 mg), Fr-C (contained Hirsutellones C and B, 153 mg). Fr-A was subjected to preparative HPLC using a reversed-phase column (Prep Nova-Pak HR C18, 6 μm, 40×100 mm) with acetonitrile/$H_2O$=75:25 as eluent at a flow rate of 20 ml/min to yield Hirsutellone A (76 mg; retention time, 18 min). Preparative HPLC (acetonitrile/$H_2O$=65:35) of Fr-B provided Hirsutellone C (14 mg; retention time, 19 min). Trituration of Fr-C in methanol (1 ml, stirred for 5 h) gave a colorless solid of Hirsutellone B (92.0 mg). The filtrate was subjected to preparative HPLC (acetonitrile/$H_2O$=65:35) to obtain Hirsutellone B (36 mg; retention time, 16 min) and Hirsutellone C (2 mg; retention time, 19 min).

The physcio-chemical characteristics of Hirsutellones A, B and C, isolated from the fungus *Hirsutella nivea* BCC 2594, are described below:

Hirsutellone A
1. Appearance: colorless solid
2. Melting point: 155-157° C.
3. Specific rotation: $[\alpha]^{29}_D$=+168° (c0.20, MeOH)
4. High resolution MS (ESI-TOF): m/z 444.2183 [M–H]$^-$ (calcd for $C_{28}H_{30}NO_4$ 444.2175)
5. UV absorption spectrum (MeOH): $\lambda_{max}$ (log ε) 203 (4.42), 228 sh (3.72), 281 sh (2.99) nm (FIG. 1).
6. IR absorption spectrum (KBr): $\nu_{max}$ 3473, 2920, 1769, 1726 (sh), 1702, 1505, 1359, 1239, 1192 cm$^{-1}$ (FIG. 2).
7. $^1$H-NMR spectrum (CDCl$_3$, 400 MHz): δ 8.24 (1H, brs), 7.16 (1H, dd, J=8.6, 1.8 Hz), 7.05 (1H, dd, J=8.6, 1.8 Hz), 7.02 (1H, dd, J=8.1, 2.3 Hz), 6.95 (1H, dd, J=8.1, 1.8 Hz), 5.91 (1H, d, 9.8 Hz), 5.49 (1H, ddd, J=9.7, 5.6, 2.4 Hz), 5.20 (1H, ddd, J=17.0, 10.3, 6.5 Hz), 4.98 (1H, d, J=10.0 Hz), 4.83 (1H, d, J=17.0 Hz), 4.46 (1H, dd, J=3.4, 3.3 Hz), 4.17 (1H, ddd, J=5.6, 5.4, 5.2 Hz), 3.65 (1H, dd, J=12.7, 6.5 Hz), 3.52 (1H, d, J=6.4 Hz), 3.36 (1H, dt, J=12.1, 6.0 Hz), 3.13 (1H, dd, J=10.9, 4.8 Hz), 2.41 (1H, t, J=12.4 Hz), 2.23 (1H, dt, J=1.0, 11.2 Hz), 2.13 (1H, m), 1.98 (1H, m), 1.84 (1H, m), 1.68 (1H, m), 1.48 (1H, dt, J=4.1, 11.3 Hz), 1.43 (1H, m), 1.35 (1H, dq, J=3.5, 12.3 Hz), 1.12 (1H, dq, J=4.0, 12.3 Hz), 0.96 (3H, d, J=6.6 Hz), 0.94 (1H, m), 0.73 (1H, dq, J=2.3, 11.2 Hz) (FIG. 3).
8. $^{13}$C-NMR spectrum (CDCl$_3$, 100 MHz): δ 198.6 (s), 176.2 (s), 170.2 (s), 158.6 (s), 136.9 (d), 132.8 (s), 130.7 (d), 129.9 (d), 127.7 (d), 127.4 (d), 123.8 (d), 123.3 (d), 118.6 (t), 87.1 (d), 59.9 (d), 56.0 (d), 54.2 (d), 50.5 (d), 49.6 (d), 48.0 (d), 43.1 (d), 38.02 (t), 37.97 (d), 36.6 (t), 35.6 (t), 33.2 (d), 29.4 (t), 22.5 (q) (FIG. 4).

Hirsutellone B
1. Appearance: colorless solid.
2. Melting point: 261-263° C. (dec)
3. Specific rotation: $[\alpha]^{27}_D$=+256° (c0.20, MeOH)
4. High resolution MS (ESI-TOF): m/z 446.2336 [M–H]$^-$ (calcd for $C_{28}H_{32}NO_4$ 446.2332)
5. UV absorption spectrum (MeOH): $\lambda_{max}$ (log ε) 203 (4.37), 227 sh (3.78), 276 sh (2.99) nm (FIG. 5).
6. IR absorption spectrum (KBr): $\nu_{max}$ 3405, 3647, 2917, 1708 (sh), 1683, 1670 (sh), 1508, 1241, 1093 cm$^{-1}$ (FIG. 6).
7. $^1$H-NMR spectrum (CDCl$_3$, 400 MHz): δ 7.10 (1H, dd, J=8.4, 1.7 Hz), 7.05 (1H, dd, J=8.4, 2.3 Hz), 6.91 (1H, dd, J=8.4, 1.5 Hz), 6.86 (1H, dd, J=8.3, 2.2 Hz), 6.15 (1H, brs), 5.81 (1H, d, J=9.8 Hz), 5.34 (1H, ddd, J=9.7, 4.7, 2.5 Hz), 5.22 (1H, dt, J=18.8, 9.6 Hz), 4.92 (1H, dd, J=16.7, 1.4 Hz), 4.86 (1H, m), 4.84 (1H, m), 3.50 (1H, m), 3.45 (1H, dd, J=11.0, 5.9 Hz), 3.00 (1H, d, J=13.0 Hz), 2.94 (1H, dd, J=12.3, 3.7 Hz), 2.86 (1H, d, J=13.0 Hz), 2.70 (1H, dd, J=14.9, 3.7 Hz), 2.16 (1H, m), 2.13 (1H, m), 1.96 (1H, m), 1.94 (1H, dd, J=14.8, 12.6 Hz), 1.85 (1H, m), 1.64 (1H, m), 1.47 (1H, dt, J=4.6, 11.5 Hz), 1.43 (1H, m), 1.41 (1H, dq, J=3.3, 12.5 Hz), 1.12 (1H, dq, J=3.5, 12.5 Hz), 0.96 (3H, d, J=6.6 Hz), 0.90 (1H, m), 0.82 (1H, dq, J=2.4, 11.1 Hz) (FIG. 7).
8. $^{13}$C-NMR spectrum (CDCl$_3$, 100 MHz): δ 200.9 (s), 172.1 (s), 158.3 (s), 137.3 (d), 131.7 (d), 131.4 (d), 128.7 (d), 127.5 (s), 127.2 (d), 121.8 (d), 121.5 (d), 116.4 (t), 89.1 (s), 84.5 (d), 55.7 (d), 54.0 (d), 50.0 (d), 48.9 (d), 47.2 (d), 46.7 (t), 44.0 (d), 42.4 (d), 38.0 (t), 36.5 (t), 34.5 (t), 33.1 (d), 29.4 (t), 22.5 (q) (FIG. 8).

Hirsutellone C
1. Appearance: colorless solid
2. Melting point: 234-235° C. (dec)
3. Specific rotation: $[\alpha]^{29}_D$=+129° (c0.20, MeOH)
4. High resolution MS (ESI-TOF): m/z 460.2121 [M–H]$^-$ (calcd for $C_{28}H_{30}NO_5$ 460.2124).
5. UV absorption spectrum (MeOH): $\lambda_{max}$ 203 (4.42), 230 (3.93), 277 (3.12) nm (FIG. 9).
6. IR absorption spectrum (KBr): $\nu_{max}$ 3396, 3264, 2921, 1713, 1698 (sh), 1687 (sh), 1507, 1241, 1134, 923 cm$^{-1}$ (FIG. 10).
7. $^1$H-NMR spectrum (CDCl$_3$, 400 MHz): 7.10 (1H, d, J=8.4 Hz), 6.98 (2H, s), 6.93 (1H, d, J=8.4 Hz), 6.00 (1H, d, J=2.2

Hz), 5.88 (1H, d, J=9.9 Hz), 5.39 (1H, ddd, J=9.8, 3.9, 2.9 Hz), 5.23 (1H, dt, J=16.9, 1.6 Hz), 4.94 (1H, dd, J=16.4, 1.6 Hz), 4.91 (1H, dd, J=9.7, 1.6 Hz), 4.63 (1H, dd, J=3.8, 3.6 Hz), 3.82 (1H, m), 3.72 (1H, dd, J=12.0, 5.9 Hz), 3.69 (1H, d, J=2.4 Hz), 3.18 (1H, d, J=13.3 Hz), 3.14 (1H, d, J=13.3 Hz), 2.15 (1H, m), 2.12 (1H, m), 2.01 (1H, m), 1.85 (1H, m), 1.71 (1H, dt, J=4.4, 11.8 Hz), 1.65 (1H, m), 1.44 (1H, m), 1.41 (1H, dq, J=3.7, 12.3 Hz), 1.11 (1H, m), 0.97 (3H, d, J=6.4 Hz), 0.94 (1H, m), 0.90 (1H, m) (FIG. 11).

8. $^{13}$C-NMR spectrum (CDCl$_3$, 100 MHz): δ 199.5 (s), 167.8 (s), 158.6 (s), 138.0 (d), 131.9 (d), 131.1 (d), 128.9 (d), 127.1 (d), 126.2 (s), 122.2 (d), 119.5 (d), 116.7 (t), 84.5 (s), 82.9 (d), 65.4 (d), 58.5 (s), 55.7 (d), 49.8 (d), 49.7 (d), 45.8 (d), 44.0 (t), 41.6 (d), 41.4 (d), 37.9 (t), 36.5 (t), 33.1 (d), 29.3 (t), 22.5 (q) (FIG. 12).

Example 2

Preparation of Hirsutellones by Fermentation of *Trichoderma* sp. BCC 7579

Background This fungus was isolated from a decaying pod of *Entada perseatha* (Leguminosae) collected in Thailand and deposited at the Thailand BIOTEC Culture Collection as BCC 7579 on Oct. 5, 2000.

The fungus was identified as a *Trichoderma* anamorph of *Hypocrea gelatinosa* (Tode: Fr.) Fr. The fungus is identified as *Trichoderma* by the following morphological characteristics: greenish pustules or tuffs of colonies, an identical branching of conidiophores, flask-shaped conidiogenous cells, and one-celled conidia in a dark green slimy drop. The phylogenetic analysis, using the internal transcribed spacers (ITS) sequence, also supports placing the fungus in the taxon *Trichoderma*.

Growth and Colony Characteristics Colonies on Difco Cornmeal Agar at 20° C. after 7 days were translucent, with scant submerged mycelium, forming numerous small conidiogenous fascicles with slimy heads of conidia, with no pigmentation in agar and no distinctive odor. Colony radius on this medium at 20° C. after 2 days measured 0.8-1.7 cm ($\bar{x}$=1.3 cm, n=10), after 3 days measured 3.0-3.7 cm ($\bar{x}$=3.5 cm), and after 4 days measured 4.4-5.2 cm ($\bar{x}$=4.7 cm).

Colonies on Difco Potato Dextrose Agar at 20° C. after 7 days were floccose with conidia forming in green flat pustules, and in dark green slimy drops around the margin of the colony, no pigmentation in agar and no distinctive odor. Colony radius at 20° C. on this medium after 2 days was 0.9-1.8 cm ($\bar{x}$=1.3 cm, n=10), after 3 days it was 4.4-5.4 cm ($\bar{x}$=4.8 cm), and after 4 days it was 5.9-6.4 cm ($\bar{x}$=6.1 cm).

Colonies on Difco Malt Extract Agar at 20° C. after 7 days were floccose with conidiation arranged in loosely ill-defined pustules, no pigmentation in agar and no distinctive odor. Colony radius at 20° C. on this medium after 2 days was 1.4-1.8 cm ($\bar{x}$=1.5 cm, n=10), after 3 days it was 3.4-3.6 cm ($\bar{x}$=3.5 cm), and after 4 days it was 4.8-5.2 cm ($\bar{x}$=5.0 cm).

(B) Morphological characteristics The hyphae are hyaline and 2-9 µm in diameter. The chlamydospore is restricted to submerged in mycelium, subhylaine, solitary, terminal or intercalary, ellipsoidal to subglobose or obovoid, and 8-10 µm in diameter. The conidiophores are hyaline, smooth-walled, and 3-5 µm wide for the most part. Thie structure is branching once or twice, singly or in pairs, at more or less acute angles and usually curved toward the apex; each branch terminating in a penicillus of 2-5 closely appressed phialides. The phialides arise in closely appressed whorls, sometimes in pairs or singly, straight or slightly curved, lageniform to ampulliform or subulate, base constricted, swollen in the middle, attenuate at tip, and measure 7-10×2.0-3.5 µm ($\bar{x}$=8.7×2.7 µm, n=15). The conidia are green, smooth-walled, ellipsoidal, 3.5-5.0× 3.5-4.5 µm ($\bar{x}$=4.4×3.9 µm, n=35), and coalesce into a large gloeoid masses.

Conidiophore branching of this fungus is similar to those of *Trichoderma crassum*, *Trichoderma flavofuscum*, *Trichoderma virens*, *Trichoderma* anamorph of *Hypocrea gelatinosa*, *Hypocrea psychrophila* and some anamorphs of *Hypocrea* subsection *Creopus* (especially *Hypocrea argillacea* and *Hypocrea luteo-viren*). However, this *Trichoderma* has green and ellipsoidal conidia which differ from the *Trichoderma* anamorph of *Hypocrea psychrophila* that has colourless conidia and differ from the *Trichoderma* anamorphs of *Hypocrea argillacea* and *Hypocrea luteo-viren* that have sub-cylindrical conidia. *Trichoderma crassum* has nonfertile conidiophore elongation while *Trichoderma flavofuscum* has brown conidiation rather than green which differs from this fungus. *Trichoderma virens* has effuse conidiation but this fungus has conidiation with conidiophores arranged in loosely flat pustules or small irregular fascicles.

The conidiation and conidiophore branching of this fungus superficially resemble those of the *Trichoderma* anamorph of *Hypocrea gelatinosa*. The molecular phylogenetics also support placing this fungus in this taxon as the ITS sequence of this fungus and those of *Hypocrea gelatinosa* are most closely related. This fungus therefore is identified as the *Trichoderma* anamorph of *Hypocrea gelatinosa*.

Experimental Procedures BCC 7579 was maintained on Potato Dextrose Agar at 25° C. for 16 days, which was cut into pieces (1×1 cm), and inoculated into 2×250 ml Erlenmeyer flasks containing 25 ml of Difco™ Potato Dextrose Broth (PDB; composition, potato starch 4.0 g, dextrose 20.0 g, per liter) (12 pieces for each flask). After incubation at 25° C. for 8 days on a rotary shaker (200 rpm), each primary culture was transferred into a 1 liter Erlenmeyer flask containing 250 ml of the same liquid medium (PDB), and incubated at 25° C. for 8 days on a rotary shaker (200 rpm). Each 25 ml portion of the secondary cultures (in 2 flasks) was transferred into 20×1 liter Erlenmeyer flasks each containing 250 ml of PDB, and static fermentation was carried out at 25° C. for 41 days.

The cultures were filtered and the residue (mycelial cake) was extracted with methanol (500 ml, room temp., 2 days). After filtration, H$_2$O (100 ml) was added to the filtrate, washed with hexane (500 ml), and the aqueous methanol layer was concentrated under reduced pressure. The residual oil was dissolved in ethyl acetate (1000 ml), washed with H$_2$O (200 ml), and concentrated to obtain a brown gum (1.73 g). This mycelial extract was passed through a Sephadex LH-20 column (3×25 cm; methanol/dichloromethane=50:50 as eluent).

Fractions containing Hirsutellones were combined (0.93 g) and subjected to column chromatography on silica gel (methanol/dichloromethane, step gradient elution) to obtain Hirsutellone A (355 mg), Hirsutellone C (59 mg), and Hirsutellone B (198 mg). Hirsutellones B and C were further purified, independently, by preparative HPLC using a reversed-phase column (Prep Nova-Pak HR C18, 6 µm, 40×100 mm) with acetonitrile/H$_2$O=60:40 as eluent at a flow rate of 20 ml/min: Hirsutellone B, yield 155 mg; Hirsutellone C, yield 46 mg.

Results Physico-chemical characteristics of Hirsutellones A, B and C, isolated from the fungus *Trichoderma* sp. BCC 7579, were identical in all respects to those described above for strain BCC 2594.

Example 3

Antituberculous Activity of Hirsutellones

Preparation of Mycobacteria *Mycobacterium tuberculosis* $H_{37}Ra$ strain (ATCC 25166) was grown in 100 ml of Middlebrook 7H9 broth supplemented with 0.2% glycerol, 1.0 g/l of casitone, 10% OADC, and 0.05% Tween 80. The complete medium was referred to as 7H9GC-Tween. The bacteria were incubated in 500-ml flasks on a rotary shaker at 200 rpm and 37° C. until the optical density at 550 nm reached 0.4-0.5. The bacteria were washed twice with phosphate-buffered saline and then suspended in 20 ml of phosphate-buffered saline. The suspension was passed through an 8-µm-pore-size filter to eliminate clumps. The number of bacteria in the filtrates were counted by plating the bacteria in Middlebrook 7H10 agar. The filtrates were stored at −80° C.

Microplate Alamar Blue Assays (MABA) Anti-tuberculous testing was performed in a 96-well microplate as previously described (Collins, L. and Franzblau, S. G., Antimicrob. Agents Chemother., 41:1004-1009 (1997)). Outer perimeter wells were filled with sterile water to prevent dehydration of the test wells. Crude extracts were initially diluted with dimethyl sulfoxide, and then were diluted to a concentration of 400 µg/ml in Middlebrook 7H9 medium containing 0.2% V/V glycerol and 1.0 g/l casitone (7H9GC). The wells in rows B to G in columns 2, 4, 5, 6, 8, 9, 10 of the microplate were filled with 100 µl of 7H9GC. The wells in column 11 were inoculated with 200 µl of the medium to serve as media controls (M). Bacteria (only) controls (B) were set-up in column 10. One hundred microliters of each crude extract solution (400 µg/ml) were added to three wells in one row in columns 2 (or 6), 3 (or 7) and 4 (or 8). One hundred microliters were transferred from column 4 (or 8) to column 5 (or 9), the contents of the wells in column 5 (or 9) were mixed well and then 100 µl of mixed medium were discarded. The wells in columns 2 and 6 served as test sample controls.

Frozen bacterial inocula were diluted 1:200 in 7H9GC medium. One hundred microliters of the bacteria were added to the wells in rows B to G in columns 3 (or 7), 4 (or 8), 5 (or 9) and 10, resulting in final bacterial titers of approximately $5 \times 10^4$ CFU/ml. The wells in column 10 served as bacteria (only) controls (B). Final concentrations of extracts were 200, 100 and 50 µg/ml in columns 3 (or 7), 4 (or 8) and 5 (or 9), respectively.

The plates were sealed with Parafilm and were incubated at 37° C. for 5 days. At day 6 of incubation, 20 µl of Alamar Blue reagent and 12.5 µl of 20% Tween 80 were added to well B10 (B) and B11 (M). The plates were re-incubated at 37° C. for 24 h. Wells were observed at 24 h to observe the color change from blue to pink. If the B wells became pink by 24 h, reagent was added to the entire plate. If the well remained blue, the additional M and B wells were tested daily until a color change occurred at which time reagents were added to all remaining wells. The microplates were resealed with Parafilm and were then incubated at 37° C. The results were recorded 24 h after adding reagent.

Blue color in the well was interpreted as no growth, reflecting the activity of the test compound in the well. A pink color was scored as growth and reflected the lack of activity of the test compound. A few wells appeared violet after 24 h of incubation, but they invariably changed to pink after extra day of incubation and thus were scored as growth (while the adjacent blue wells remained blue).

The activity of a compound was tested in a second plate containing the compound two-fold serially diluted from 50 µg/ml, and the results were recorded as the minimal inhibitory concentration (MIC).

MIC values of the Hirsutellones and standard antituberculous drugs, kanamycin and isoniazid, are as follows:

| Compound | MIC (µg/ml) |
| --- | --- |
| Hirsutellone A | 0.78 |
| Hirsutellone B | 0.78 |
| Hirsutellone C | 0.78 |
| kanamycin | 2.5 |
| isoniazid | 0.04 |

The Hirsutellones strongly inhibit the growth of *Mycobacterium tuberculosis* in vitro.

Example 4

Cytotoxicity of Hirsutellones

Hirsutellones A, B and C were tested for cytotoxicity by incubating with Vero cells (African green monkey kidney cell line from American Type Culture Collection USA; ATCC # CCL-81). Each compound was dissolved in dimethyl sulfoxide and then diluted in the culture medium of the Vero cells (Eagle's Minimum Essential with 10% heat-inactivated fetal bovine serum and antibiotics). The Vero cells and the compound were incubated together in a 96-well microplate at a cell concentration of $1.9 \times 10^4$ cells/190 µl/well, in a $CO_2$ incubator at 37° C. for 3 days.

The numbers of the cells in the wells were then determined by a staining method (Skehan, P., et al., J. Natl Cancer Inst., 82:1107-1112 (1990)). The cells were initially fixed by 50% cold trichloroacetic acid (TCA) at 4° C. for 30 minutes. The cells were then washed with water 4 times. After drying, the cells were stained with 0.05% sulforhodamine B in 1% acetic acid for 30 minutes, washed with 1% acetic acid 4 times and dried at room temperature. Finally, 10 mM Tris-base pH 10 was added. The absorbance at 510 nm of test wells was measured by an ELISA microplate reader. The absorbance was proportionate to the number of the viable cells in the wells. The toxicity level of the compound was recorded as the concentration that rendered the number of viable cells to be less than half of the negative control wells, which contained the cells with DMSO but not the compound. Ellipticine was used as a positive control. The toxicity level of each compound against Vero cells was expressed as $IC_{50}$.

Hirsutellones were also tested for cytotoxicity against multiple human cancer cell lines, to study the effects on human cells in vitro. The cancer cell lines included KB cells (oral epidermoid carcinoma; ATCC # CCL-17), BC cells (breast cancer) and NCI-H187 cells (lung cancer; ATCC # CRL-5804) The same protocol as that for the cytotoxicity assay against Vero cells was used, except for the starting compound concentration which was 20 µg/ml.

The $IC_{50}$ values of Hirsutellones A, B and C, and ellipticine (standard compound) are as follows:

| Compound | Cytotoxicity, IC$_{50}$ (µg/ml) | | | |
| --- | --- | --- | --- | --- |
| | Vero | KB | BC | NCI-H187 |
| Hirsutellone A | >50 | >20 | >20 | >20 |
| Hirsutellone B | >50 | >20 | >20 | 6.0 |
| Hirsutellone C | 12 | 4.6 | 3.2 | 8.3 |
| Ellipticine | 0.40 | 1.3 | 1.5 | 0.39 |

The Hirsutellones strongly inhibit the growth of *Mycobacterium tuberculosis,* but show weak or no cytotoxicity, especially Hirsutellone A which has an excellent selectivity index. Therefore these compounds may be useful in the treatment of tuberculosis.

What is claimed is:

1. A compound, Hirsutellone A, wherein the compound has the formula:

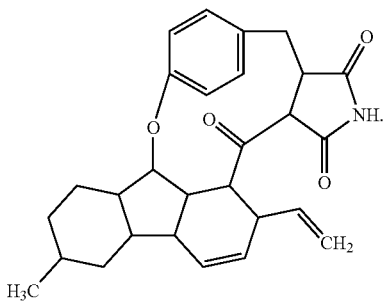

2. A composition comprising the compound of claim 1.

3. The composition of claim 2 wherein the composition is a pharmaceutical composition.

4. A method of isolating the compound of claim 1 comprising:
   fermenting a liquid culture of a fungus containing mycelia;
   obtaining said mycelia from said culture;
   extracting said mycelia with an organic solvent to produce an extract; and
   separating said extract to produce said compound.

5. The method of claim 4 wherein said mycelia are isolated by filtration, and said extract is separated by gel filtration or chromatography.

6. The method of claim 4 wherein the fungus is the strain BCC 2594 or BCC 7579.

7. The method of claim 6 wherein said mycelia are isolated by filtration, and said extract is separated by gel filtration or chromatography.

8. A method of treating tuberculosis in a subject, the method comprising administering to said subject an effective amount of the pharmaceutical composition of claim 3.

9. A compound, Hirsutellone B, wherein the compound has the formula:

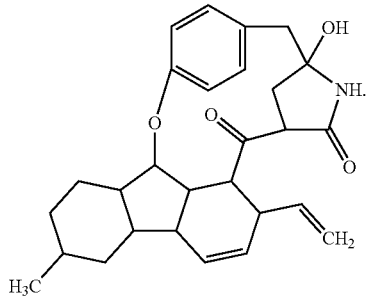

10. A composition comprising the compound of claim 9.

11. The composition of claim 10 wherein the composition is a pharmaceutical composition.

12. A method of isolating the compound of claim 9 comprising:
    fermenting a liquid culture of a fungus containing mycelia;
    obtaining said mycelia from said culture;
    extracting said mycelia with an organic solvent to produce an extract; and
    separating said extract to produce said compound.

13. The method of claim 12 wherein said mycelia are isolated by filtration, and said extract is separated by gel filtration or chromatography.

14. The method of claim 12 wherein the fungus is the strain BCC 2594 or BCC 7579.

15. The method of claim 14 wherein said mycelia are isolated by filtration, and said extract is separated by gel filtration or chromatography.

16. A method of treating tuberculosis in a subject, the method comprising administering to said subject an effective amount of the pharmaceutical composition of claim 11.

17. A compound, Hirsutellone C, wherein the compound has the formula:

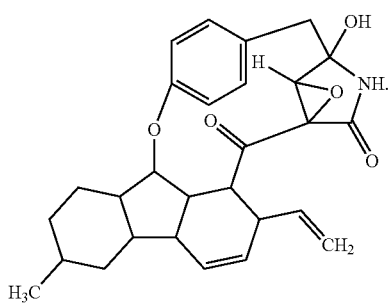

18. A composition comprising the compound of claim 17.

19. The composition of claim 18 wherein the composition is a pharmaceutical composition.

20. A method of isolating the compound of claim 17 comprising:
    fermenting a liquid culture of a fungus containing mycelia;
    obtaining said mycelia from said culture;
    extracting said mycelia with an organic solvent to produce an extract; and
    separating said extract to produce said compound.

21. The method of claim 20 wherein said mycelia are isolated by filtration, and said extract is separated by gel filtration or chromatography.

22. The method of claim 20 wherein the fungus is the strain BCC 2594 or BCC 7579.

23. The method of claim 22 wherein said mycelia are isolated by filtration, and said extract is separated by gel filtration or chromatography.

24. A method of treating tuberculosis in a subject, the method comprising administering to said subject an effective amount of the pharmaceutical composition of claim 19.

* * * * *